United States Patent

Saini et al.

[11] Patent Number: 5,349,181
[45] Date of Patent: Sep. 20, 1994

[54] FIBER OPTIC CHEMICAL SENSOR HAVING SPECIFIC CHANNEL CONNECTING DESIGN

[75] Inventors: Devinder P. Saini, Henderson, Nev.; Tommy J. Law, Tempe, Ariz.

[73] Assignee: FCI-FiberChem, Inc., Las Vegas, Nev.

[21] Appl. No.: 98,125

[22] Filed: Jul. 26, 1993

[51] Int. Cl.⁵ .............................................. N01J 5/16
[52] U.S. Cl. ............................ 250/227.14; 250/227.24; 385/12
[58] Field of Search ............... 250/227.21, 227.28, 250/227.14–227.19, 227.24; 385/12

[56] References Cited

U.S. PATENT DOCUMENTS

| | | | |
|---|---|---|---|
| 4,275,296 | 6/1991 | Adolfsson | 250/227.21 |
| 4,644,154 | 2/1987 | Brogardh et al. | 250/227.21 |
| 4,929,049 | 3/1990 | Goullon et al. | 385/12 |
| 5,026,139 | 6/1991 | Klainer et al. | 385/12 |
| 5,094,958 | 3/1992 | Klainer et al. | 250/227.23 |
| 5,149,963 | 9/1992 | Hassler, Jr. | 250/227.21 |

Primary Examiner—David C. Nelms
Assistant Examiner—Stephone B. Allen
Attorney, Agent, or Firm—Henry P. Sartorio

[57] ABSTRACT

In a sensor assembly, an optical fiber with a sensing region is connected at one end through a fiber guide tube to a detector housing containing a sensing detector. At the other end the fiber is connected through a fiber guide tube to a light source which has a reference detector mounted laterally thereto. The sensing and reference detectors are a matched pair of the same type. The guide tube in the source has a bevelled end which reflects a portion of light from the source to the reference detector.

10 Claims, 3 Drawing Sheets

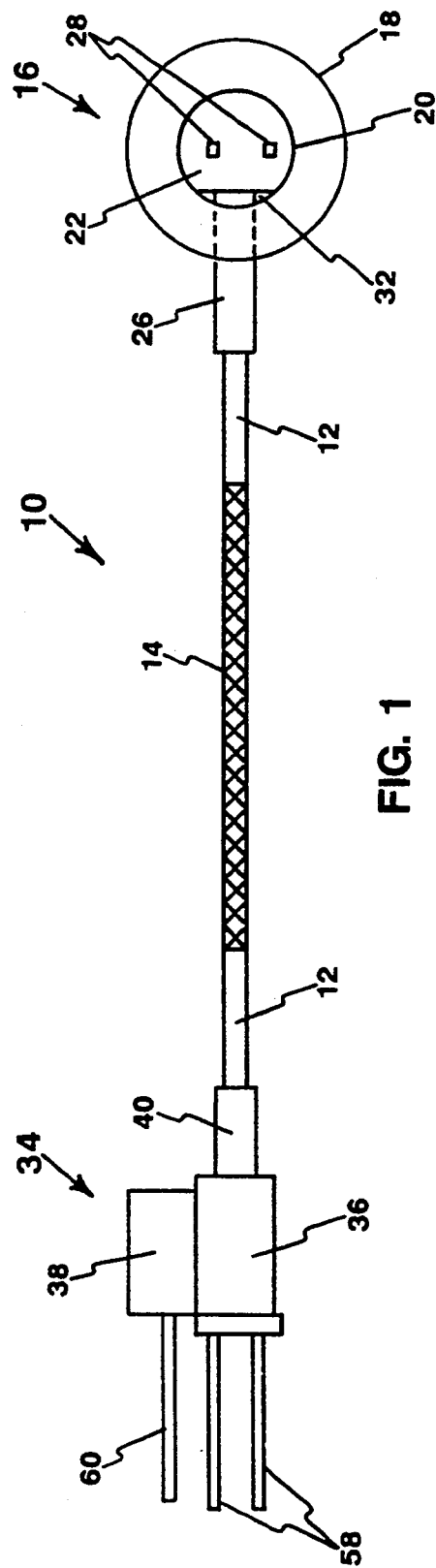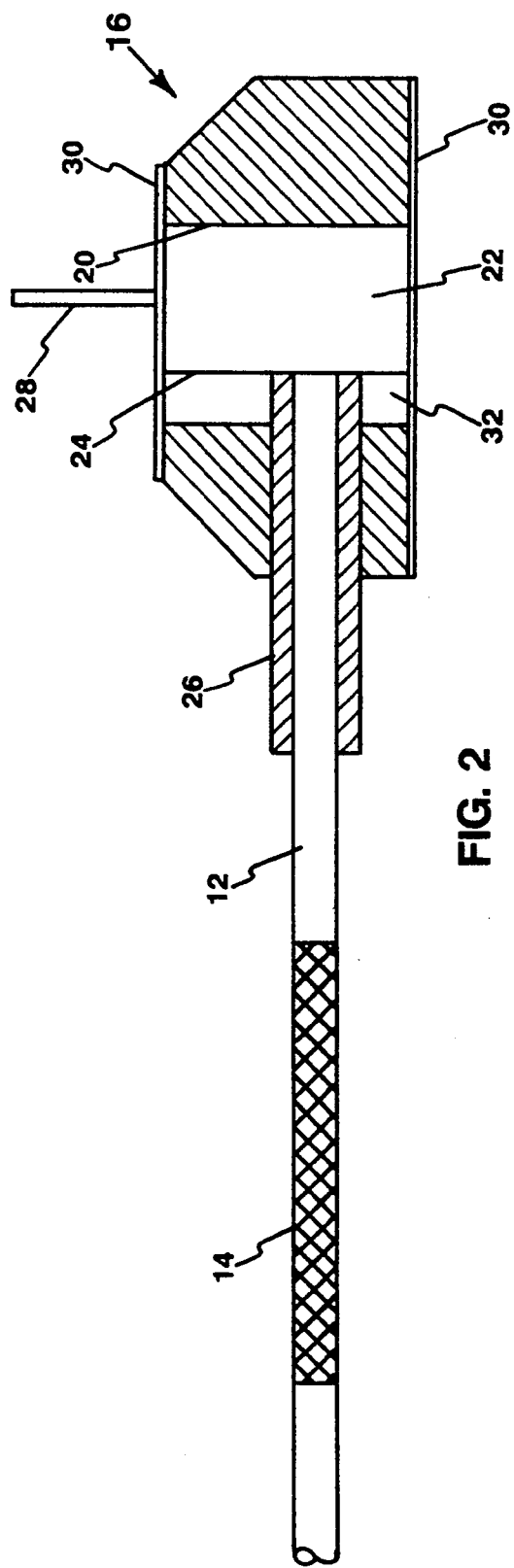

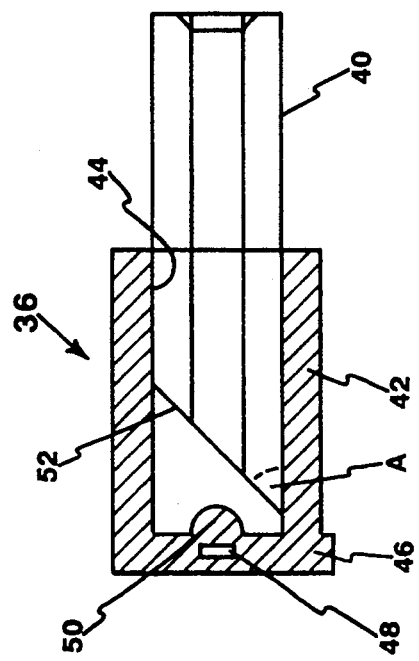
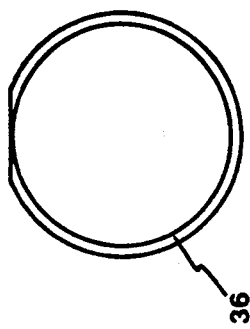
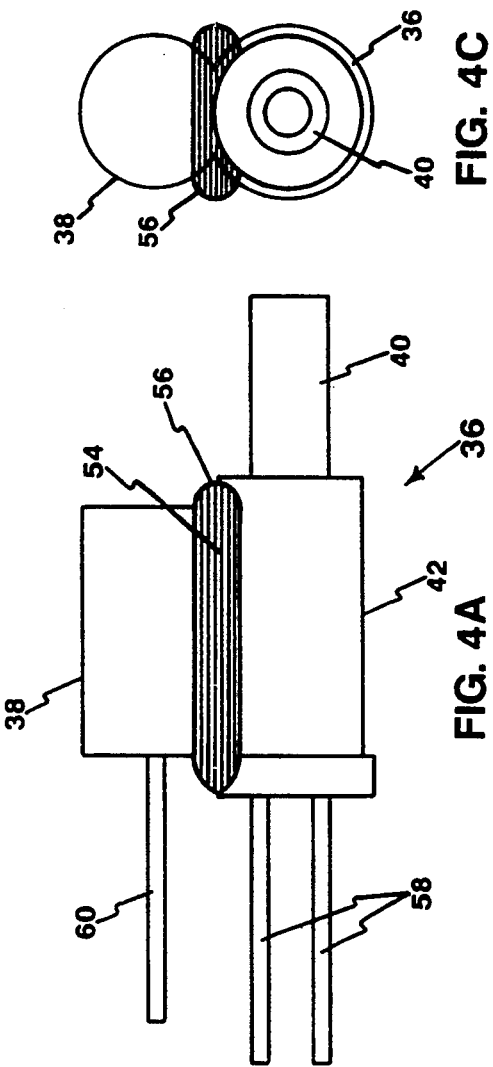
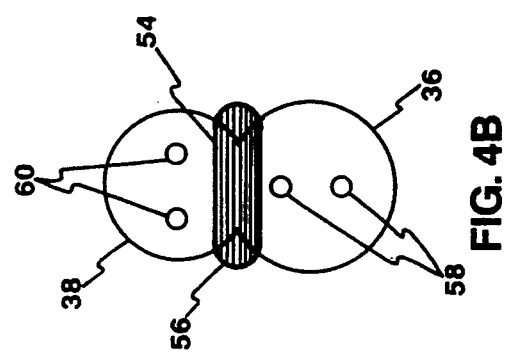

5,349,181

FIBER OPTIC CHEMICAL SENSOR HAVING SPECIFIC CHANNEL CONNECTING DESIGN

BACKGROUND OF THE INVENTION

The invention relates generally to optical chemical sensors and more particularly to fiber optic chemical sensors.

A wide variety of optical chemical sensors, have been proposed to measure a variety of chemical species. For example, U.S. Pat. Nos. 4,929,049 and 5,026,139 to Klainer, et al describe chemical sensors for hydrocarbons using thin film metal clads on an optical fiber.

However, to develop a practical, reliable sensor for long-term field use requires a sensor configuration which eliminates problems of variations in the components, particularly the source, due to aging, temperature changes, etc. The output of the sensor should vary only as a function of the species being detected and not because of variations in internal or external factors. U.S. Pat. No. 5,094,958 to Klainer et al shows one approach which produces two responses, only one of which is analyte specific. The other only depends on external factors so the ratio is self-compensating.

SUMMARY OF THE INVENTION

The invention is a fiber optic chemical sensor design in which a source, detector and reference detector are configured to allow for compensation of source variations due to aging, temperature and the like. The sensor detector is mounted in a housing and coupled to one end of the optical fiber through a fiber guide tube. A reference detector is mounted on a lateral surface of the source. The distal end of the fiber is coupled to the source through a second fiber guide tube. The second guide tube has a bevelled end to reflect a portion of the light from the source into the laterally mounted reference detector. The distal end of the fiber is positioned in the second guide tube at a distance from the source selected to produce a predetermined ratio of sensor detector/reference detector signals. Since the signals from the two detectors will be ratioed, any variations in the detector signals caused by variations in the source will cancel out, and changes in the ratio will be a true measure of changes in the chemical species to be detected.

BRIEF DESCRIPTION OF THE DRAWINGS

FIG. 1 is a side view of the entire assembly.

FIG. 2 is a sectional view of the sensor detector housing.

FIG. 3 is a sectional view of the source with integral housing and bevelled fiber guide tube.

FIGS. 4A, 4B are side and end views of the reference detector mounted to the source housing.

DETAILED DESCRIPTION OF THE PREFERRED EMBODIMENTS

Figure 5:
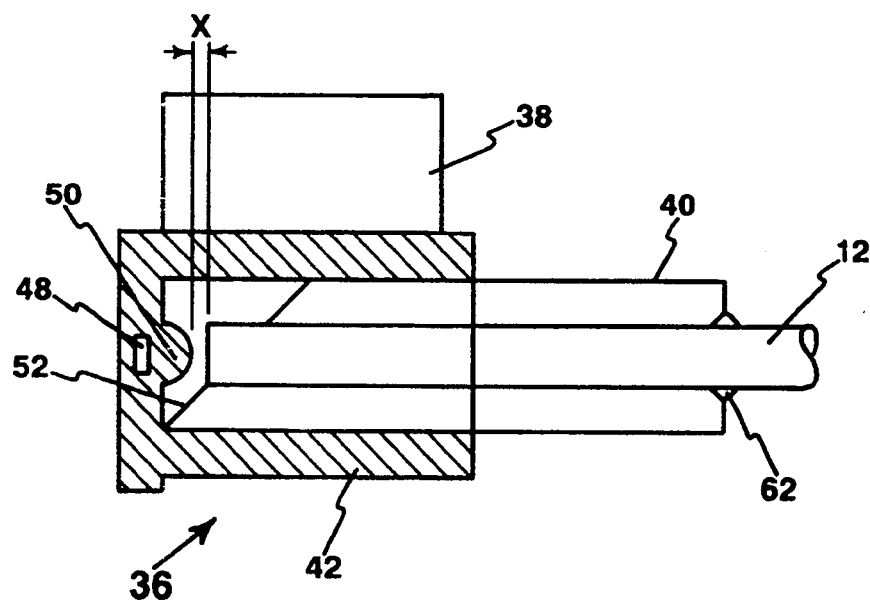
FIG. 5 is a sectional view of the positioning of the fiber relative to the source in the bevelled guide tube.

As shown in FIG. 1, sensor assembly 10 is formed of a length of optical fiber 12 having a species sensing coating or active region 14 formed on a portion thereof. The coating 14 may be a thin film metal clad for a refractive index type sensor useful for detecting hydrocarbons, as described in U.S. Pat. Nos. 4,929,049 and 5,026,139, which are herein incorporated by reference. The coating 14 may also be any other type of species-specific sensing chemistry.

One end of fiber 12, as shown in FIGS. 1 and 2, is optically coupled to detector subassembly 16 which is formed of detector housing 18 (e.g., made of plastic) which contains a channel 20 therein for mounting a detector 22. Detector 22 is preferably a photodiode, e.g., Siemens photodiode #SFH206. Detector 22 has a flat radiant sensitive surface 24. A fiber guide tube 26 (e.g. made of metal or plastic) communicates or extends through housing 18 so that fiber 12 can be optically aligned with surface 24 of detector 22. The end of tube 26 contacts surface 24 and the tube 26 is oriented perpendicular to surface 24. The end of fiber 12 is inserted through tube 26 until it contacts surface 24 and is then glued or otherwise fastened in place. Electrical leads 28 extend from detector 22 out of housing 18. The top and bottom of housing 18 and detector 22 are covered with an optical isolation layer 30 so that external light cannot reach detector 22, e.g., through gap 32.

As shown in FIG. 1, the opposite end of fiber 12 is optically coupled to source/reference subassembly 34 which is formed of a source 36 and a laterally mounted orthogonally oriented reference detector 38, detector 38 is preferably a photodiode of the same type as detector 22 (e.g., Siemens photodiode #SFH206). A fiber guide tube 40 communicates with or extends into source 36 so that fiber 12 is optically aligned with source 36.

As shown in FIG. 3, source 36, preferably an LED (e.g., Siemens Transmitter Diode #SFH450), is formed of an integral housing 42 defining a channel 44 therein and a base portion 46 containing the light emitting region 48 and a lens 50 aligned therewith. Fiber guide tube 40 fits into channel 44. The end of tube 40 is cut at a 45° angle A so that the bevelled edge 52 forms a reflective surface (annular ring) which reflects a portion of the light from source 36 substantially at right angles to the light transmitted through tube 40. This reflected light is input into the reference detector to provide a reference signal. Source housing 42 is optically transparent.

As shown in FIGS. 4A,B reference detector 38 is mounted to a lateral surface of source 36, i.e., to housing 42. Reference detector 38 is identical to sensor detector 22 and has a flat radiant sensitive surface 54 which contacts housing 42. Detector 38 is attached to source 36 by suitable means, e.g., epoxy 56. Thus reference detector 38 is oriented perpendicularly to source 36 (and sensing detector 22). The bevelled surface 52 of FIG. 3 provides the means to split the light from the source and input a portion into detector 38. Electrical leads 58, 60 extend from source 36 and detector 38. Housing 42 may also be covered by an optical isolation layer.

The end of fiber 12 must be correctly positioned with respect to source 36, as illustrated in FIG. 5. Tube 40 with bevelled end 52 is positioned within housing 42 so that some source light is input into reference detector 38. Tube 40 aligns fiber 12 with light emitting region 48 and lens 50. However, the spacing X can be varied to control the amount of light which is input into fiber 12. In operation, the sensor detector output is compared to the reference detector signal, i.e., a ratio is formed to compensate for variations in the source. The two detectors are matched, i.e., they are identical components. Thus variations in the ratio will be due only to variations in the species being detected. Therefore, the sensor configuration is designed with a predetermined detector/reference ratio. The fiber 12 is moved in tube 40 until this preselected ratio of values is obtained (with no detected species present) and then fixed in place, e.g., by epoxy 62.

In accordance with the invention, the source, detector and reference detector are configured so that variations in the source can be eliminated from sensor measurements. The sensor assembly along with signal processing electronics and external probe housing form a complete probe.

Changes and modifications in the specifically described embodiments can be carried out without departing from the scope of the invention which is intended to be limited only by the scope of the appended claims.

What is claimed is:

1. A fiber optic chemical sensor, comprising:
    an optical fiber having a sensing region formed on a portion thereof;
    a sensing detector housing defining a channel therein;
    a sensing detector mounted in said sensing detector housing channel;
    a first fiber guide tube extending into said sensing detector housing and communicating with said channel formed therein; wherein one end of said fiber extends into said first tube and is optically aligned with said sensing detector;
    a light source having a channel formed therein and a light emitting region aligned with said channel;
    a second fiber guide tube extending into said source channel; wherein the opposed end of said fiber extends into said second tube and is optically aligned with said source;
    a reference detector mounted laterally on said source for receiving a portion of light emitted from said source.

2. The sensor of claim 1 wherein said second tube further comprises a bevelled end for reflecting said light from said source to said reference detector.

3. The sensor of claim 2 wherein said bevelled end is formed at a 45° angle to the tube axis.

4. The sensor of claim 1 wherein said sensing and reference detectors are identical detectors.

5. The sensor of claim 1 wherein said source further comprises an optically transparent integral housing defining said source channel.

6. The sensor of claim 1 wherein said source is an LED and said sensing and reference detectors are photodiodes.

7. The sensor of claim 1 wherein said sensing and reference detectors are matched photodiodes.

8. The sensor of claim 1 wherein the end of said fiber which extends into said second tube is positioned at a distance from said light emitting region of said light source so that the outputs of said sensing and reference detectors have a preselected ratio.

9. The sensor of claim 1 wherein said source further comprises an integral lens optically aligned with said light emitting region.

10. The sensor of claim 1 further comprising an optical isolation layer formed on said sensing detector housing to optically isolate said sensing detector from external light sources.

* * * * *